United States Patent [19]

Epstein et al.

[11] Patent Number: 4,840,911
[45] Date of Patent: Jun. 20, 1989

[54] USE OF SULFOXIDES FOR TESTING IONIZATION DETECTOR SYSTEM

[75] Inventors: Joseph Epstein, Baltimore; John A. Parsons, Abingdon; Frank Block, Edgewood, all of Md.

[73] Assignee: The United States of America as represented by the Secretary of the Army, Washington, D.C.

[21] Appl. No.: 55,811

[22] Filed: May 28, 1987

[51] Int. Cl.⁴ .......................................... G01N 31/00
[52] U.S. Cl. ........................................ 436/8; 436/9
[58] Field of Search .............. 436/8, 19, 173; 422/98; 250/281, 282, 283, 286, 287

[56] References Cited

U.S. PATENT DOCUMENTS 4,551,624 11/1985 Spangler et al. ................. 422/98

Primary Examiner—Barry S. Richman
Assistant Examiner—T. J. Wallen
Attorney, Agent, or Firm—Robert P. Gibson; Edward Goldberg; Edward F. Costigan

[57] ABSTRACT

A method of simulating a positive response by volatile organophosphorus esters to an ionization detector system which comprises forwarding to the ionization detector system a gaseous stream comprising water vapor and a di(lower alkyl) sulfoxide or a cyclic sulfoxide represented by the formula I:

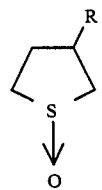

wherein R is hydrogen or a lower alkyl group, in an amount sufficient to elicit a positive response by the ionization detector system.

3 Claims, No Drawings

USE OF SULFOXIDES FOR TESTING IONIZATION DETECTOR SYSTEM

The invention described herein may be manufactured, used and licensed by or for the Government for governmental purposes without payment of any royalties thereon or therefor.

BACKGROUND OF THE INVENTION

This invention relates to the use of sulfoxides such as dimethyl sulfoxide or tetramethylene sulfoxide to simulate a positive response of volatile organophosphorus esters to an ionization detector system.

An ionization detector system has been developed as an alarm system to selectively respond to volatile chemical agents in the atmosphere, such as toxic organophosphorus esters, for example, iso-propoxymethylphosphoryl fluoride (hereinafter "GB"), pinacolymethylphosphoryl fluoride (hereinafter "GD") or O-ethyl S-(2-diiso-propylamino)ethyl methylphosphonothioate (hereinafter "VX").

It would be desirable to test periodically the ionization detector alarm system by use of relatively nontoxic volatile chemical reagents which would simulate the response of the toxic organophosphorus esters to the ionization detector system.

SUMMARY OF THE INVENTION

In accordance with this invention, there is provided a method of simulating a positive response by volatile organophosphorus esters to an ionization detector system which comprises forwarding to the ionization detector system a gaseous stream comprising water vapor and a di(lower alkyl) sulfoxide or a cyclic sulfoxide represented by the formula I:

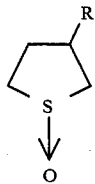

wherein R is hydrogen or a lower alkyl group, in an amount sufficient to elicit a positive response by the ionization detector system.

DETAILED DESCRIPTION OF THE INVENTION

As used herein, by the term "volatile organophosphorus esters" is meant the toxic volatile derivatives of methylphosphonic acid including GB, GD, and derivatives of methyldichlorophosphine such as VX. GB and GD may be prepared by reaction of methylphosphonyl difluoride with iso-propyl alcohol and pinacolyl alcohol, respectively. VX may be prepared by conversion of methyl dichlorophosphine into ethyl-(2-diiso-propylamino)ethyl methylphosphonate which, in turn, is mixed with a sulfur source to form VX.

By the term "lower alkyl" as used herein is meant straight and branched chain alkyl groups of one to six carbon including methyl, ethyl, propyl, butyl, pentyl, hexyl and the corresponding branched-chain isomers thereof such as iso-propyl, tert- or sec-butyl, iso-valeryl and iso-hexyl.

Typical suitable di(lower alkyl) sulfoxides include dimethyl sulfoxide, diethyl sulfoxide, di-n-propyl sulfoxide, diiso-propyl sulfoxide, di-n-butyl sulfoxide, di-sec-butyl sulfoxide, di-n-pentyl sulfoxide, di-n-hexyl sulfoxide, methyl ethyl sulfoxide, and n-propyl sec-butyl sulfoxide. Di(lower alkyl) sulfoxide are commerically available but may be prepared by oxidation of the corresponding sulfide with, for example, meta-chloroperbenzoic acid.

Typical suitable cyclic sulfoxides represented by the formula I include tetramethylene sulfoxide, 3-methyl-, 3-ethyl, 3-n-propyl-, 3-n-butyl, 3-n-pentyl, or 3-n-hexyl-tetramethylene sulfoxide. Tetramethylene sulfoxide is commerically available. The 3-substituted tetramethylene sulfoxides may be prepared by peracid oxidation of the corresponding 3-(lower alkyl) substituted tetramethylene sulfide which is conveniently obtained by a catalytic reduction of the corresponding 3-(lower alkyl) substituted thiophene. For example, the 3-(lower alkyl) substituted thiophenes can be prepared by contact of the appropriate alkadiene with sulfur for a short time at elevated temperatures. Thus, isoprene (2-methylbutadiene) is contacted with sulfur for about 2 seconds at 566° C. to form 3-methylthiophene.

The instrument known as an ionization detector system operates at or near atmospheric pressure to detect trace (10 to 100 ppb) toxic impurities, e.g., GB, GD, or VX in a moist air stream. The moist air stream, heated to about 60° C. (the normal operating temperature of the system) is pumped into the system and passes over a source of ionization radiation, normally a beta-ray source, such as titanium tritide coated foil. The ionized air contains primary ions ($N_2^+$, $O_2^+$, and $O_2^-$) formed near the beta-ray source by electron impact or attachment. A sequence of ion-molecule reactions follow and equilibrium between ionic clusters is rapidly established. The mixture of air and ions is drawn through a series of baffles to a detector in the form of a Faraday Cup ion collector. On the end of the Faraday Cup is a grid to allow the air to exit. The beta-ray source is in electrical contact with a center manifold stud and can be biased either positively, negatively, or maintained at zero potential with respect to the collector. The collector responds to the ions by producing a current which is conveniently measured by a picoammeter. Compounds, such as volatile toxic organo-phosphorus esters and the sulfoxides useful in this invention elicit a positive response at the collector part of the ionization detector system. By the term "positive response", as used herein in reference to compounds such as the sulfoxides useful in this invention, is meant an ion current produced at the collector by the ionized gaseous stream containing water and a sulfoxide. The ion current produced should be easily and reproducibly measured compared to the background at compund concentrations of less than about 100 parts per billion (ppb).

Volatile toxic organophosphorus esters such as GB, GD, and VX are sensitively detected by the ionization detector system in that (1) GB, GD, or VX produce a signal of about 2 to 4 volts at concentrations of less than about 100 ppb, and (2) there is a reasonably linear relationship between the signal and the concentration of, for example, GB, GD, or VX.

The sulfoxides useful in the present invention also are sensitively detected by the ionization system.

To practice the method of this invention, trace concentrations (less than 100 ppb) of the sulfoxides useful in this invention are prepared in a continuous flow by using air dilution of the vapor from the sulfoxides of interest and water vapor.

Based on the response of known concentrations of dimethyl sulfoxide, diethyl sulfoxide, and tetramethylene sulfoxide (at constant flow rates), we have shown that there exists a linear relationship between the logarithm of the concentration of the ions reaching the detector (and hence the current) and the inverse of the square root of the molecular weight of the sulfoxide. Each of the three above-listed sulfoxides followed this linear relationship, and produced an ion current at the picoammeter of the ionization detector system equivalent to a 3 volt response.

The concentrations of other sulfoxides useful in this invention required to give a positive response of 3 volts are shown in Table I hereinbelow. Based on the data for the sulfoxides useful in this invention, the calculated concentrations of GB, GD, and VX which would be expected to give a positive response of about 3 volts are 4.8, 3.4, and 1.2 ppb, respectively. In making these calculations, it is assumed that the sulfoxide oxygen and phosphoryl oxygen have similar basicities and that, therefore, a sulfoxide and organophosphonate ester of the same molecular weight would give the same quantitative response at the ionization detector of this invention. In an actual test using the ionization detector system described hereinabove, a concentration of GB of 6.4 ppb gave a voltage reading of $2.2\pm0.2$ volts, a concentration of 6.0 ppb of GD gave a voltage reading of $4.0\pm0.2$ volts, and a concentration of VX of 1.7 ppb gave a voltage reading of $3.7\pm0.2$ volts.

Thus, the sulfoxides useful in this invention are excellent substitutes for the toxic organophosphorus ester in the ionization detector system. The sulfoxides useful in the present invention gave a positive response in the ionization detector system described hereinabove that is both qualitatively and quantitatively equivalent to the behavior of organophosphorus esters including GB, GD, and VX.

TABLE I

| Compound | Molecular Weight (g/mole) | Concentration (ppb) |
|---|---|---|
| $(C_2H_5)_2SO$ | 106 | 10.4 |
| $(C_3H_7)_2SO$ | 134 | 4.8 |
| $(C_4H_9)SO$ | 162 | 3.2 |

TABLE I-continued

| Compound | Molecular Weight (g/mole) | Concentration (ppb) |
|---|---|---|
| $(CH_2)_4SO$ | 104 | 4.4 |

The selection of the sulfoxide to use for testing the ionization detector system for response to a particular organophosphorus ester will depend upon the sensitivity desired. The sulfoxide should have a vapor pressure at the temperature for testing the ionization detector alarm system so as to produce a concentration in the vapor state which will give an acceptable positive response at the detector. Thus, under arctic conditions, one should select a cyclic sulfoxide of the formula I, whereas, in tropical climates, one should select one of the many di(lower alkyl) sulfoxides useful in this invention. The physical properties of the sulfoxides (vapor pressure, molecular weight) provides a basic for limiting the size of the di(lower alkyl) groups and lower alkyl group, R, in the sulfoxides useful in this invention.

Trace concentrations of samples of the sulfoxides may be prepared by air dilution of the sulfoxide of interest. The concentration of water vapor in the gaseous stream forwarded to the ionization detector system should be at least about 3 ppm.

What is claimed is:

1. A method of simulating a positive response of organophosphorus esters to an ionization detector system which comprises forwarding to the ionization detector system a gaseous stream comprising water vapor and a sulfoxide selected from the group consisting of a di (lower alkyl) sulfoxide or a cyclic sulfoxide the latter represented by the formula I:

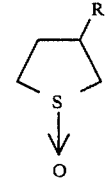

2. A method according to claim 1 wherein the sulfoxide is a di (lower alkyl) sulfoxide and the di (lower alkyl) sulfoxide is diethyl sulfoxide.

3. A method according to claim 1 wherein the sulfoxide is a cyclic sulfoxide and the cyclic sulfoxide is tetramethylene sulfoxide.

* * * * *